United States Patent [19]

Orvik

[11] Patent Number: 4,594,422

[45] Date of Patent: Jun. 10, 1986

[54] SELECTIVE HALOGENATION OF 6-HYDROXY PICOLINE DERIVATIVES

[75] Inventor: Jon A. Orvik, Concord, Calif.

[73] Assignee: The Dow Chemical Company, Midland, Mich.

[21] Appl. No.: 710,262

[22] Filed: Mar. 11, 1985

[51] Int. Cl.⁴ .............................................. C07D 211/84
[52] U.S. Cl. ..................................... 546/303; 546/345
[58] Field of Search ................................. 546/303, 345

[56] References Cited

U.S. PATENT DOCUMENTS 3,859,295  1/1975  Schroder et al. .................. 546/303

*Primary Examiner*—Henry R. Jiles
*Assistant Examiner*—J. Richter
*Attorney, Agent, or Firm*—S. Preston Jones; Ronald G. Brookens

[57] ABSTRACT

The invention relates to a method for selective halogenation of 6-hydroxy picoline derivatives such as 6-hydroxy picolinic acid and 6-hydroxy picoline. When 6-hydroxy picolinic acid is halogenated by allowing it to stand in an aqueous mineral acid solution for a sufficient period to replace the halo substituent with a hydroxy substituent, and then halogenated, an improved yield of the 3-halo, 6-hydroxy picolinic acid to the 5-halo 6-hydroxy picolinic acid is obtained.

8 Claims, 1 Drawing Figure

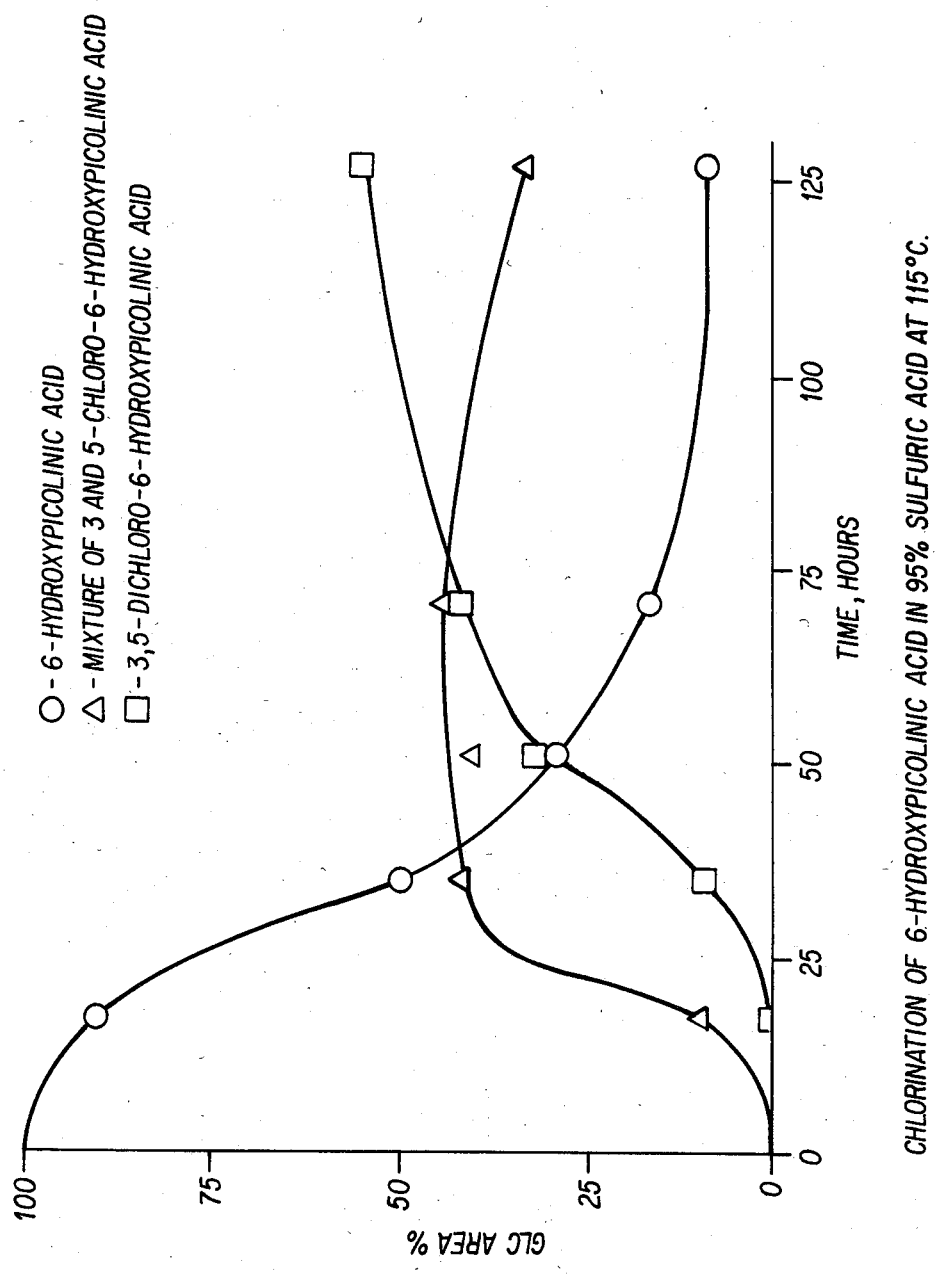

SELECTIVE HALOGENATION OF 6-HYDROXY PICOLINE DERIVATIVES

BACKGROUND OF THE INVENTION

1. Field of the Invention

The present invention relates to a process for halogenating 6-hydroxy picoline derivatives in the 3-position. The process is accomplished by allowing a 6-halo picoline derivative to stand in an aqueous mineral acid solution for a sufficient period to replace the halo substituent with a hydroxy substituent, and halogenating the aqueous mineral acid solution of 6-hydroxy picoline derivative to produce the corresponding 3-halo 6-hydroxy picoline derivative.

2. Description of the Prior Art

In current technology, as exemplified by U.S. Pat. No. 4,217,185, the process arrives at the product 3,6-dichloropicolinic acid, which is known as Lontrel ®, through a reduction process comprising passing a D.C. current to a cathode from an anode through an aqueous basic solution of tetrachloro-2-picolinic acid in order to obtain the products 3,4,6- and 3,5,6-tricholoro-2-picolinic acids, which can further be reduced to 3,6-dichloro picolinic acid.

U.S. Pat. No. 4,087,431 pertains to a process for preparing 3,6-dichloropicolinic acid by (a) reacting 3,5,6-trichloro-4-hydrazino-picolinic acid with a basic reagent at temperatures of from 60° C. to reflux for a period of one-half to three hours; (b) acidifying the mixture with a mineral acid to a pH of about 1, and recovering the product.

U.S. Pat. No. 4,334,074 discloses a process for recovering 3,6-dichloro picolinic acid from basic aqueous solution by acidification with HCl and a flocculant, separating said acid, extracting the unprecipitated acid from the mother liquor with a solvent, and stripping the extracted acid from the solvent with a separate portion of the basic feed solution.

SUMMARY OF THE INVENTION

It is an object of the present invention to provide a selective process for halogenating a 6-hydroxy picoline derivative in the 3-position to produce the corresponding 3-halo-6-hydroxy picoline derivative product.

High ratios of the 3-chloro-6-hydroxy picolinic acid to the 5-chloro-6-hydroxy picolinic acid are obtained.

Another object of the invention is to provide a method for selective halogenation of 6-hydroxy picolinic acid in the 3-position to obtain increased yields or ratios of 3-halo, 6-hydroxy picolinic acid to the 5-halo 6-hydroxy picolinic acid.

A further object is to provide a process for selective halogenation of the 6-hydroxy picolinic acid in the 3-position to obtain a 5:1 ratio of the 3-halo, 6-hydroxy picolinic acid to the 5-halo 6-hydroxy picolinic acid.

A yet further object to the invention is to provide a method for selective halogenation of 6-hydroxy-picoline in the 3-position, to obtain 3-halo-6-hydroxypicoline.

These and other objects of the invention are accomplished by allowing a 6-halo picoline derivative to stand in an aqueous mineral acid solution for a sufficient period of time to replace the halo substituent with a hydroxy substituent, and halogenating the aqueous mineral acid solution of the 6-hydroxy picoline derivative to obtain the corresponding 3-halo 6-hydroxy picoline product.

Now the invention will be described in detail with reference to the preferred embodiments.

BRIEF DESCRIPTION OF THE INVENTION

In an attempt to chlorinate 6-chloropicolinic acid to determine the ratio of the 3-chloro to the 5-chloro product produced (Equation 1), it was found that the starting material had hydrolyzed to 6-hydroxypicolinic acid by long standing in 54% sulfuric acid. It was discovered that the 6-hydroxy picolinic acid chlorinated (Equation 2) to give a mixture of mono and dichlorinated products.

However, in the case of the mono chlorinated materials, the product ratio of the 3-chloro to 5-chloro 6-hydroxypicolinic acid was found to be 5 to 1.

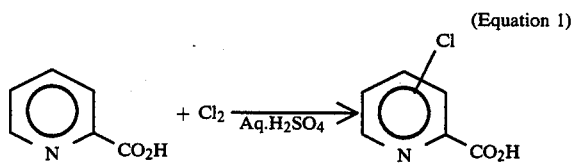

(Equation 1)

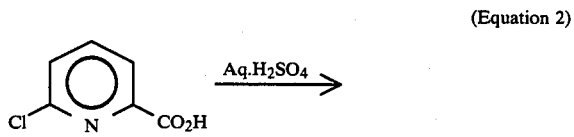

(Equation 2)

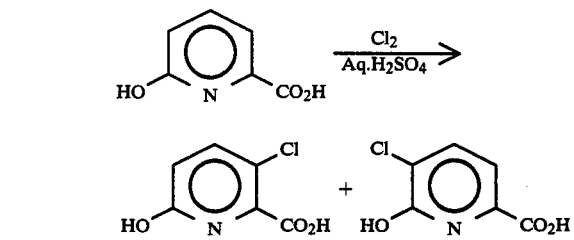

Since the 3-chloro-6-hydroxypicolinic acid is a potential precursor for Lontrel ®, this finding is both surprising and commercially significant.

®Trademark of The Dow Chemical Company—3,6-dichloropicolinic acid.

The 6-hydroxy picoline derivative—6-hydroxypicoline has also been found to chlorinate selectively in the 3-position, and the product, 3-chloro-6-hydroxypicoline can be converted to the 3,6-dichloropicoline. This latter material can then be converted to the acid or Lontrel ®(3,6-dichloropicolinic acid), either by oxidation of the methyl group or by subsequent chlorination and hydrolysis.

DETAILED DESCRIPTION OF THE INVENTION

EXAMPLE 1

A sample of 4.7 g of 6-hydroxypicolinic acid was added along with 25 g of 95% sulfuric acid and excess chlorine to a glass pressure bottle. The mixture was placed in a 115° C. oil bath and stirred magnetically. The reaction was interrupted occasionally by cooling the mixture in dry ice in order to open the bottle and remove a sample of the contents for gas-liquid chromatography (glc) analysis. The bottle was then reclosed and replaced in the hot oil bath.

The accompanying graph of the FIGURE represents the course of reaction with time. The identities of the peaks in the glc were determined by combination glc-mass spectrum and by spiking in known samples made by entirely different methods.

The following table represents the results of a liquid chromatogram (HPLC) of the product obtained in Example 1. Unlike the gas chromatogram, the liquid chromatogram separates the two monochloro isomers of interest.

| Peak | Time Min. | Area % | Identity |
|------|-----------|--------|----------|
| 1 | 4.00 | 20.8 | 3-chloro-6-hydroxypicolinic acid |
| 2 | 5.34 | 4.2 | 5-chloro-6-hydroxypicolinic acid |
| 3 | 8.56 | 70.7 | 3,5-dichloro-6-hydroxypicolinic acid |

The identities were determined by doing a separate chromatogram for a known sample of 5-chloro-6-hydroxypicolinic acid (retention time: 5.33 min), and by spiking a known sample of the 3-chloro-6-hydroxypicolinic acid into the reaction mixture and observing a large increase in the area of peak 1 of the FIGURE (rentention time 4.04 min,).

EXAMPLE 2

Chlorination of 6-Hydroxypicoline

In a 6 oz pressure bottle, 6-hydroxy-alpha-picoline (10.9 g, 0.10 mols) was dissolved in 65 g of 67% sulfuric acid. The homogeneous solution was cooled in a dry ice bath and approximately 4 g (0.06 mols) of chlorine was condensed into the mixture. The bottle was sealed (magnetic stirring) and placed in a 130° C. oil bath for 16 hrs. The contents were then diluted with ice and water and brought to neutrality with sodium hydroxide. This resulted in a precipitate which was collected and washed with water, and then dried in an oven overnight. 9.5 g of a grey solid was obtained. The solid was analyzed by glc (BSA derivative) and found to contain two peaks in the ratio of 4.8 to 1. No starting material was detected. By analyzing these peaks further by combination glc-mass spectrum, the larger first peak was identified as having the correct molecular weight for monochlorohydroxypicoline and the second peak was identified similarly as dichlorohydroxypicoline.

In order to determine if there was more than one isomer of the monochlorohydroxypicoline in the single glc peak, a sample of the solid product was treated with phosphorus oxychloride ($POCl_3$), which converted the hydroxy group to a chloro group.

Known samples of both 3,6-dichloro and 5,6-dichloro-alpha-picoline were available and were shown to separate on the glc column used. The only dichloro-alpha-picoline peak observed in the glc of the $POCl_3$-treated material corresponded to the 3,6-dichloro-alpha-picoline. No peak was observed for the 5,6 isomer.

The glc mass-spectrum of $POCl_3$-treated material also confirmed that the molecular weight of the aforementioned peak did have a correct mass for a dichloromethylpyridine. A substantial amount of the dichlorohydroxy-alpha-picoline also was converted by $POCl_3$ to a trichloro-alpha-picoline showing that the $POCl_3$ reaction could not have been selective in converting one of the monochloro-hydroxy derivatives over the other.

Thus, it was concluded that the monochlorination of 6-hydroxy-alpha-picoline is greater than 98% selective to the 3-position.

The operable temperature range is not deemed critical and the halogenation reaction proceeds from 25° to 200° C., however, the preferred temperature range for the reaction is from 75° to 150° C.

While the examples illustrate some preferred embodiments of the present invention utilizing chlorine as the halogenating gas, it is to be understood that the invention can be practiced with equal facility employing bromine as the halogenating material, due to the similarity of reactivity between these halogens.

What is claimed is:

1. A process for selective halogenation of a 6-hydroxy picoline derivative in the 3-position comprising:

Allowing a 6-halo picoline derivative selected from the group consisting of 6-halo picolinic acid and 6-halo picoline to stand in an aqueous mineral acid solution for a sufficient period to replace the halo substituent with a hydroxy substituent, and halogenating the aqueous mineral acid solution of said 6-hydroxy picoline derivative to obtain the corresponding 3-halo 6-hydroxy picoline product.

2. The process of claim 1, wherein the halogenation proceeds at temperatures ranging from 25° to 200° C.

3. The process of claim 2, wherein the halogenation proceeds at temperatures ranging from 75° to 150° C.

4. The process of claim 1, wherein the halogenating gas is selected from chlorine and bromine.

5. The process of claim 1, wherein the mineral acid is sulfuric acid.

6. The process of claim 1, wherein said picoline derivative is 6-chloro picolinic acid, said halogenating material is chlorine, and the corresponding product is a mixture of 3-chloro-6-hydroxy picolinic acid and 5-chloro-6-hydroxy picolinic acid.

7. The process of claim 1, wherein said picoline derivative is 6-hydroxy picoline, said halogenating material is chlorine, and the corresponding product is 3-chloro-6-hydroxypicoline.

8. The process of claim 6, wherein the mixture of 3-chloro-6-hydroxy picolinic acid to 5-chloro-6-hydroxy picolinic acid is in a ratio of 5:1.

* * * * *